US006277874B1

(12) United States Patent
Crutcher et al.

(10) Patent No.: US 6,277,874 B1
(45) **Date of Patent: *Aug. 21, 2001**

(54) METHODS FOR THE TREATMENT OF APOLIPOPROTEIN E RELATED DISEASES

(75) Inventors: Keith A. Crutcher; Judith A. K. Harmony, both of Cincinnati, OH (US)

(73) Assignee: University of Cincinnati and Apologic, Incorporated, Cincinnati, OH (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/255,331

(22) Filed: Feb. 22, 1999

Related U.S. Application Data

(63) Continuation of application No. 09/214,742, filed as application No. PCT/US97/11836 on Jul. 8, 1997.

(60) Provisional application No. 60/021,405, filed on Jul. 9, 1996.

(51) Int. Cl.[7] .......................... A61K 31/425; A61K 31/38; A61K 31/34

(52) U.S. Cl. .......................... 514/367; 514/446; 514/470; 514/576

(58) Field of Search .......................... 530/324, 359; 435/212, 11; 514/369, 54, 446, 59, 62, 576, 597, 470; 436/69.6

(56) References Cited

U.S. PATENT DOCUMENTS

| | | | | |
|---|---|---|---|---|
| 3,000,787 | * | 9/1961 | Bianchini | 514/167 |
| 4,956,347 | * | 9/1990 | Ban et al. | 514/54 |
| 5,182,364 | * | 1/1993 | Dyer et al. | 530/324 |
| 5,525,472 | * | 6/1996 | Lifshitz et al. | 435/69.6 |
| 5,672,685 | * | 9/1997 | Matthew et al. | 530/359 |
| 5,770,609 | * | 6/1998 | Grainger et al. | 514/319 |
| 5,795,860 | * | 8/1998 | Witt et al. | 514/12 |
| 5,814,472 | * | 9/1998 | Miki et al. | 435/11 |
| 5,910,437 | * | 6/1999 | Kent et al. | 435/212 |

FOREIGN PATENT DOCUMENTS

| | | | | |
|---|---|---|---|---|
| 9801101 | * | 1/1998 | (WO) | A61K/37/02 |

OTHER PUBLICATIONS

Clay et al., Localization of a Domain in Apolipoprotein E . . . , Biochemistry, vol. 34, 11142–11151, 1995.*

Crutcher(Clay) et al. Neurite Degeneration Elicited . . . , Esperimental neurology, vol. 130, pp. 120–126, 1994.*

Benezra et al., Antiproliferative activity . . . , Arterioscler. Thromb. vol. 14/12, pp. 1992–1999, (1994).*

* cited by examiner

*Primary Examiner*—William R. A. Jarvis
*Assistant Examiner*—Vickie Kim
(74) *Attorney, Agent, or Firm*—Harness, Dickey & Pierce P.L.C.

(57) ABSTRACT

Methods for treating diseases associated with toxicity of Apolipoprotein E ("apoE"). Specifically, the present invention relates to new methods for treating a mammal having a condition associated with toxicity of apolipoprotein E cleavage fragments containing residues 130–169, comprising administering to said mammal a pharmacologically effective amount of compound or a pharmaceutically acceptable sale, derivative or fragment thereof to interfere with the receptor-binding site associated with residues 130–169 of the apolipoprotein E molecule in said mammal.

23 Claims, No Drawings

METHODS FOR THE TREATMENT OF APOLIPOPROTEIN E RELATED DISEASES

RELATED APPLICATION

This is a continuation-in-part of U.S. Ser. No. 09/214,742, filed Sep. 10, 1999, which claims priority from international application PCT/US97/11836, filed Jul. 8, 1997, which is a continuation-in-part of U.S. Ser. No. 60/021,405, filed Jul. 9, 1996, all hereby expressly incorporated by reference.

SPONSORSHIP

The U.S. Government has a paid-up license in this invention and the right in limited circumstances to require the patent owner to license others on reasonable terms as provided for by the terms of Grant No. RO1 HL27333, NS31410 and R43 NS37986-01 awarded by the National Institutes of Health.

BACKGROUND OF THE INVENTION

The present invention relates generally to a method for treating diseases associated with toxicity of Apolipoprotein E ("apoE"). Specifically, the present invention is a new method for treating a mammal having a condition associated with toxicity of apolipoprotein E and/or apolipoprotein E cleavage fragments containing residues 130–169, comprising administering to said mammal a pharmacologically effective amount of a compound or a pharmaceutically acceptable salt, derivative or fragment thereof to interfere with the toxicity mechanism associated with residues 130–169 of the apolipoprotein E molecule in said mammal.

Alzheimer's disease is the most common form of both senile and pre-senile dementia in the world and is recognized clinically as relentlessly progressive dementia that presents with increasing loss of intellectual function including memory and disturbances in speech (Merritt, *A Textbook of Neurology*,. 6th edition, pp. 484–489 Lea & Febiger, Philadelphia (1979)). The disease itself usually has a slow and insidious progress that affects both sexes equally, worldwide. It begins with mildly inappropriate behavior, uncritical statements, irritability, a tendency towards grandiosity, euphoria and deteriorating performance at work; it progresses through deterioration in operational judgment, loss of insight, depression and loss of recent memory; it ends in severe disorientation and confusion, apraxia of gait, generalized rigidity and incontinence (Gilroy & Meyer, *Medical Neurology,* pp. 175–179 MacMillan Publishing Co. (1979)) Alzheimer's disease afflicts an estimated four million human beings in the United States alone at a cost of 100 billion dollars a year (Schumock, G. T., *J. Health Syst. Pharm.* 55(52): 17–21 (1998); Hay & Ernst, *Am. J. Public Health,* 77: 1169–1175 (1987)). It is found in 10% of the population over the age of 65 and 47% of the population over the age of 85 (Forsyth, *E., Phys. Ther.* 78:1325–1331 (1998); Evans et al., *JAMA* 262:2551–2556 (1989)). In addition, the disease is found at much lower levels in the younger age groups, usually beginning at about 30 years of age and even rarely in late childhood (Adams & Victor, *Principles of Neurology*, pp. 401–407 (1977)).

The etiology of Alzheimer's disease is unknown. Evidence for a genetic contribution comes from several important observations such as the familial incidence, pedigree analysis, monozygotic and dizygotic twin studies and the association of the disease with Down's syndrome (for review see Baraitser, *The Genetics of Neurological Disorders,* 2nd edition, pp. 85–88 (1990)). Nevertheless, this evidence is far from definitive and it is clear that one or more other factors are also required.

In recent years, research has suggested that apolipoprotein E ("apoE") plays a potential role in the pathogenesis of Alzheimer's disease. Apolipoprotein E performs various functions as a protein constituent of plasma lipoproteins, including its role in cholesterol metabolism. It was first identified as a constituent of liver-synthesized very low density lipoproteins ("VLDL") which activity is the transport of triglycerides from the liver to peripheral tissues. ApoE is instrumental in lipoprotein metabolism in several ways (Mahley, et al., *J. Lipid Res.* 25:1277–1294 (1984)). It is a recognition site for several cellular lipoprotein receptors, including hepatocyte receptors for chylomicron and VLDL remnants (Hui, et al., *J. Biol. Chem.,* 259:860–869 (1984); Shelburne, et al., *J. Clin. Invest.,* 65:652–658 (1980)).

Apo E-enriched lipoproteins have also been described to have a function in the immune system by inhibiting mitogen- or antigen-stimulated lymphocyte proliferation in vitro and in vivo. In the ovary, apo E inhibits androgen production by LH-stimulated cultured theca and interstitial cells (Dyer, et al., J. Biol. Chem., 263:10965 (1988)).

Further substantiation that apo E and apo B-containing lipoproteins are important regulators of lymphocyte function has come from studies of the inhibitory properties of fetal cord blood plasma lipoproteins (Curtiss, et al., *J. Immunol.,* 133:1379 (1984)). In these studies a direct correlation between apo E and inhibition was established.

There are three major isoforms of ApoE, referred to as ApoE2, ApoE3 and ApoE4 which are products of three alleles at a single gene locus. Three homozygous phenotypes (Apo-E2/2, E3/3, and E4/4) and three heterozygous phenotypes (ApoE3/2, E4/3 and E4/2) arise from the expression of any two of the three alleles. The most common phenotype is ApoE3/3 and the most common allele is E3. See Mahley, R. W., *Science* 240:622–630 (1988).

The amino acid sequences of the three types differ only slightly. ApoE4 differs from ApoE3 in that in ApoE4 arginine is substituted for the normally occurring cysteine at amino acid residue 112. The most common form of ApoE2 differs from ApoE3 at residue 158, where cysteine is substituted for the normally occurring arginine. See Mahley, *Science*, supra. ApoE phenotypes and genotypes are well described and known in the art as described above. The established nomenclature system as well as the phenotypes and genotypes for ApoE, are described in, for example, Zannis, et al., J. Lipid. Res. 23:911 et seq. (1982), which is incorporated by reference herein.

Subjects with the ApoE4/4 genotype are as much as eight times as likely to be affected by Alzheimer's disease as subjects with the ApoE2/3 or ApoE3/3 genotypes. Further, the average age of onset of Alzheimer's disease and the average age of survival is lower for those having one ApoE4 allele, and lowest for those having two ApoE4 alleles (U.S. Pat. No. 5,508,167). Thus, a subject's prognosis for Alzheimer's disease is more likely to be negative if the subject has an ApoE4 allele and most negative if the subject has more than one ApoE4 allele. The negative prognosis can be viewed in terms of increased likelihood of developing the disease, or of earlier age of onset. Other ApoE-linked diseases include type III Hyperlipidemia and atherosclerosis. Other evidence indicates that polymorphisms in the apoE promoter are also associated with increased risk of AD (Lambert et al., *Human Mol. Gen.* 7:533 (1998); Lambert et al., *Human Mol. Gen.* 7:1511 (1998)).

Studies have shown that apoE fragments ranging from 5 to 22 kDa are present n the post-mortem cerebral spinal fluid from both control patients and patients with AD. The only major band immunoprecipitated by a monoclonal antibody that recognizes the putative toxic domain runs with an apparent molecular weight of about 22 kDa . This fragment likely corresponds to the major apoE thrombin cleavage product, which has been shown to be protease-resistant. Weisgraber, et al., *J. Biol. Chem.* 258:12348–54 (1983).

Amino acids 130–169 in human apoE encompass an immunoregulatory domain with both cytostatic and cytotoxic activities against interleukin-2-dependent T cells. This finding is consistent with results of previous studies (Cardin, et al., 1988; Dyer, et al., 1991) that implicated residues 141–155 in apoE's antiproliferative effect on naive mitogen-activated T cells. The similar potencies of E130–149 and E130–155 indicate that the cytostatic domain is located within residues 130–149. However, a longer peptide representing residues 130–169 and dimeric peptides of amino acids 141–155 also have potent cytotoxic activity. These results indicate that the positively charged, leucine-rich sequence, corresponding to amino acids 141–149 (Leu-Arg-Lys-Leu-Arg-Lys-Arg-Leu-Leu; referred to as LRKLRKRLL in single letter amino acid shorthand; SEQ. ID. NO: 1) in the mature protein which represents the overlap between the functional peptides identified, is responsible for both the cytostatic and cytotoxic effect (Clay et al., *Biochemistry* 34:1 1142–51 (1995)). When tested against primary neurons in culture, these peptides were also found to elicit degeneration of neurites and neuronal cell death.

Purified apoE, derived from transfected HEK cells, subjected to thrombin cleavage and separated using gel filtration to collect the 22 kD fragment, yields enhanced toxicity when tested against primary neurons in culture. The 22 kD fragments purified from the E4 isoform are more toxic than E3-derived fragments. The putative toxic site is closely associated with one of two well-characterized apoE heparin binding domains associated with residues 141–147 of apoE.

The density of four positively charged amino acid residues in the 141–149 domain clearly make a significant contribution to apoE peptide toxicity. Consistent with this conclusion is the ablation of peptide-mediated toxicity by the polyanionic glycosaminoglycans ("GAG") heparin, heparan sulfate and chondroitin sulfate. However, GAG-binding capacity does not, in itself, account for bioactivity since peptide E211–243, which contains a second heparin-binding site but lacks the 141–149 sequence, is inactive. Furthermore, not all GAGs show inhibition of the toxicity.

While there has been considerable research into the mechanisms underlying Alzheimer's disease, there continues to be an ongoing need for new ways to investigate and combat this disorder and other diseases in which ApoE has been implicated.

U.S. Pat. No. 5,795,860 discloses protein-specific glycosaminoglycan sequences and methods of use of such sequences in blocking the action of glycan-binding proteins.

U.S. Pat. No. 4,727,063 discloses low molecular weight heparins having a sulfation degree of at least 2.5 and a molecular weight ranging from 2000 to 9000, prepared by depolymerization and sulfation with a mixture of sulfuric and chlorosulfonic acid. None has a sulfation degree up to 3.5.

U.S. Pat. No. 3,454,560 discloses a process for the depolymerization and sulfation of chondroitin sulfate by means of sulfuric acid at a concentration not lower than 85% w/w. The sulfuric acid can contain another sulfating agent, such as sulfuric anhydride or chlorosulfonic acid, but the same document specifies that, even operating in said ambient, only sulfuric acid participates in the sulfation reaction.

U.S. Pat. No. 5,508,167, Roses et al., issued Apr. 16, 1996, discloses methods of diagnosing or prognosing Alzheimer's disease in a subject. The methods involve directly or indirectly detecting the presence or absence of an apolipoprotein E type (ApoE4) isoform or DNA, encoding ApoE4 in the subject. The presence of ApoE4 indicates the subject is afflicted with Alzheimer's disease or at risk of developing Alzheimer's disease. A novel immunochemical assay for detecting the presence or absence of the Apolipoprotein E (ApoE) E4 allele in a subject is also disclosed.

U.S. Pat. No. 5,384,398, Lormeau et al., issued Jan. 24, 1995, discloses new high molecular mass N,O-sulphated heparosans consisting of chains or of a mixture of chains having a molecular mass of between $1.5\times10^4$ and $4.0\times10^6$D, characterized by a repeating disaccharide structure.

U.S. Pat. No. 5,164,295, Kisilevsky et al., issued Nov. 17, 1992, discloses a method of identifying compounds which impair and/or prevent initiation and/or progression of amyloid deposition, such compounds being useful as therapeutics for treating amyloidosis and amyloid-related disorders.

U.S. Pat. No. 4,956,347, Ban et al., issued Sep. 11,1990, relates to the use of ATEROID, a mixture of "sulfomucopolysaccharides" comprising heparin, heparan sulfate-like substance, dermatan sulfate, and chondroitin sulfate A and C, for the treatment of patients suffering from Alzheimer's-type senile dementia. ATEROID is defined in the U.S. Pat. No. 3,000,787, Bianchini, issued Sep. 19, 1961, as a heparinoid anti-cholesterolemic factor. ATEROID, which is in some aspects similar to heparin, has essentially no anti-coagulant effect. The patent discloses that ATEROID can be extracted from the small intestine and particularly from the duodenum of mammals, by means of methods suitable for the isolation of aminopolysaccharidic or glycoproteic compounds.

Snow, A. D., et al., *American Journal of Pathology*, Vol 133, No. 3, December 1988, disclose the presence of heparan sulfate proteoglycan (HSPG) in neuritic plaques associated with Alzheimer's disease. HSPG was detected in the amyloid fibrils present in neuritic plaques in the brains of Alzheimer's patients using antibodies against the protein core of HSPG. Additionally, HSPG was shown to be present in primitive plaques. It is suggested that the accumulation of HSPG in plaques takes place during early stages of plaque development.

Snow, A. D., and Kisilevsky, R., *Laboratory Investigation*, Vol. 53, No. 1, pp. 37–44 (1985), report the temporal relationship between glycosaminoglycan (GAG) accumulation and amyloid deposition during experimental amyloidosis. Using models which facilitate induction of amyloidosis, it was disclosed that amyloid-associated GAGs appear in the tissues together with the AA amyloid protein independent of the tissue type. It is suggested that the appearance of GAG in the inflammatory amyloidosis condition appears to be part of the process involved in the deposition of the AA protein.

Margolis, R. U., and Margolis, R. K., *Neurobiology of Aging*, Vol. 10, pp. 500–502 (1989) disclose various properties of nervous tissue proteoglycans with respect to their proposed relation to amyloid beta-protein in Alzheimer's disease-related amyloidosis. It is pointed out on page 501, column 1, lines 4 to 8 that the role of proteoglycans in Alzheimer's disease amyloidosis is only circumstantial and the role of proteoglycans in it is unclear. At page 502, column 2, lines 3 to 6, it is disclosed that due to the absence of firm evidence specifically linking proteoglycans to pathogenesis of Alzheimer's disease, it is premature to speculate on the relationship of proteoglycans to amyloid in degenerative processes.

Caputo, C. B., *Neurobiology of Aging*, Vol. 10, pp. 503–504 (1989) refers to the significance of binding of proteoglycans to amyloid. It is disclosed that co-localization of proteoglycans with amyloids indicates that they are binding but the consequence of such binding is unknown. The question is asked whether proteoglycans bind inadvertently to amyloid or whether the proteoglycans in binding to amyloid or its precursors lead to the formation of beta-pleated sheet conformation or the stabilization of such a conformation. It is suggested that in vitro studies be performed to determine whether Alzheimer amyloid precursor binds to proteoglycans. On page 503, column 1, last paragraph, the possibility that amyloid protein binds well to proteoglycans is raised. However, evidence is referred to which indicates otherwise.

SUMMARY OF THE INVENTION

The present invention relates generally to a method for treating diseases associated with toxicity of Apolipoprotein E ("apoE"). Specifically, the present invention is a new method for treating a mammal having a condition associated with toxicity of whole apolipoprotein E or apoE cleavage fragments containing residues 130–169, comprising administering to said mammal a pharmacologically effective amount of a compound or a pharmaceutically acceptable salt, derivative or fragment thereof which interferes with the receptor-binding site or toxicity associated with residues 130–169 of the apolipoprotein E molecule in said mammal.

In one embodiment, pharmacological composition will comprise a glycosaminoglycan or derivative or fragment thereof along with pharmaceutically acceptable carriers, fillers or excipients. The administering step may comprise administering a pharmacological composition comprising an agent selected from the group consisting of heparin, heparan sulfate, dermatan sulfate, dextran sulfate, pentosan polysulfate, polyvinyl sulfate and fragments thereof along with pharmaceutically acceptable carriers, fillers or excipients. In a second embodiment, the pharmacological composition will comprise a protease inhibitor, or a mixture of protease inhibitors along with one or more pharmaceutically acceptable carriers, fillers, or excipients. The administering step may comprise administering a pharmacological composition comprising a protease inhibitor "cocktail" such as a mixture of aprotinin, leupeptin, pepstatin and antipain all available from Sigma Chemical Co. Another embodiment will comprise a combination of the first and second embodiments.

In another embodiment, pharmacological compositions will comprise compounds containing napthaline sulfonic acids bonded to a phenyl or naphthyl group by a diazo or amide bond thereof along with pharmaceutically acceptable carriers, fillers or excipients. The administering step may comprise administering an agent such as, but not limited to, suramin sodium, ponceau S, Evan's blue, calconcarboxylic acid, Chicago sky blue 6b or mixtures thereof along with pharmaceutically acceptable carriers, fillers or excipients.

In a further embodiment, pharmacological compositions will comprise compounds having a triphenylmethane core structure comprising at least one carboxylate or sulfate substituent thereof along with pharmaceutically acceptable carriers, fillers or excipients. The carboxylate or sulfate substituents can be directly attached to the phenyl rings or can be part of a benzoic acid or benzene sulfonic acid attached to the triphenylmethane core. The administering step may comprise administering an agent such as, but not limited to, aurintricarboxylic acid, aniline blue, Coomassie brilliant blue R-250, Coomassie brilliant blue G-250, light green SF yellowish, methyl blue or mixtures thereof along with pharmaceutically acceptable carriers, fillers or excipients.

In yet another embodiment, pharmacological compositions will comprise compounds comprising tetrabromophenolsulfonpthalein along with pharmaceutically acceptable carriers, fillers or excipients. The administering step may compromise administering an agent such as, but not limited to, bromophenol blue, bromocresol green or mixtures thereof along with pharmaceutically acceptable carriers, fillers or excipients.

The method may be by oral administration of the interfering compound or a pharmaceutically acceptable salt or derivative thereof into said mammal.

The administering step comprises parenteral administration of the receptor-binding site interfering compound or a pharmaceutically acceptable salt or derivative thereof into said mammal. This administration may be by transdermal administration, subcutaneous injection, intravenous injection, intraperitoneal injection, intramuscular injection, intrasternal injection, intrathecal injection, intraventricular and intracerebroventricular injection, inhalatory spray, and infusion techniques.

The methods also comprise administering the receptor-binding site interfering compound or a pharmaceutically acceptable salt or derivative thereof along with a lipophilic solvent or carrier. The lipophilic solvent or carrier may be an organic solvent, phosphatidyl choline and cholesterol.

The present method is useful in the treatment of a variety of diseases associated with apoE toxicity including, but not limited to Alzheimer's disease and Alzheimer-related senile dementia, cerebral amyloidosis, coronary heart disease, outcome following head injury or intracerebral hemorrhage, ischemic stroke, normal pressure hydrocephalus, ischemic cerebrovascular disease in end-stage renal disease, glomerulopathy after renal transplantation, diabetic nephropathy, atherosclerosis, and HIV-associated dementia and peripheral neuropathy.

Accordingly, an object of the present invention is to provide treating a mammal having a condition associated with toxicity of apolipoprotein E cleavage fragments containing residues 130–169, comprising administering to said mammal, in need of such treatment, a pharmacologically effective amount of compound or a pharmaceutically acceptable salt, derivative or fragment thereof to interfere with generation of toxic fragments containing the receptor-binding site associated with residues 130–169 of the apolipoprotein E molecule in said mammal or to interfere with the receptor binding site itself.

The present invention has several benefits and advantages. By use of the methods described, a safe and effective treatment may be administered for a variety of diseases associated with apoE toxicity without the toxic side effects associated with many of the treatments available.

Other objects, features and advantages of the present invention will become apparent from the following detailed description. It should be understood, however, that the detailed description and the specific example, while indicating preferred embodiments of the invention, are given by way of illustration only, since various changes and modifications within the scope of the invention will become apparent to those skilled in the art from this detailed description.

DETAILED DESCRIPTION OF THE INVENTION

Apolipoprotein E (apoE), is a constituent of liver-synthesized very low density lipoproteins which function in the transport of triglycerides from the liver to peripheral tissues. It is a recognition site for several cellular lipoprotein receptors, including hepatocyte receptors for chylomicron and VLDL remnants.

The term "apoE receptor-binding site ("ARS"), refers to the binding site contained on the whole apoE protein and the 22 kDa fragment and is responsible for binding of apoE with the low density lipoprotein ("LDL") receptor or the LDL receptor-related protein (LRP) or other related receptors. The apoE receptor binding site is associated with amino acid residues 130 through 169 (Thr-Glu-Glu-Leu-Arg-Val-Arg-Leu-Ala-Ser-His-Leu-Arg-Lys-Leu-Arg-Lys-Arg-Leu-Leu-Arg-Asp-Ala-Asp-Asp-Leu-Gln-Lys-*Arg (Cys)-Leu-Ala-Val-Try-Gln-Ala-Gly-Ala-Arg-Glu-Gly; or as TEELRVRLASHLRKLRKRLLRDADDLQK-*R(C)-LAVYQAGAREG in single letter amino acid shorthand; SEQ. ID. NO: 2) in the mature protein. The sequence shown occurs in isoforms E3 and E4. The E2 isoform is identical with the exception of a cysteine substitution for arginine at position 158 denoted with an asterisk (SEQ. ID. No: 3). The ARS overlaps the apoE heparin-binding site on the apoE protein. The heparin-binding region is a positively charged, leucine-rich sequence, corresponding to amino acids 141–147 (Leu-Arg-Lys-Leu-Arg-Lys-Arg; referred to as LRKLRKR in single letter amino acid shorthand; SEQ. ID. No. 4) in the mature protein. ApoE peptides and proteins lacking these domains are not toxic to neurons.

The 22 kDa fragment of the apoE protein is the only major band immunoprecipitated from human brain and CSF samples by a monoclonal antibody that recognizes the putative toxic domain. This fragment runs with an apparent molecular weight of about 22 kDa, and likely corresponds to the major apoE thrombin cleavage product, which has been shown to be protease-resistant.

The term "biologically active" refers at least to the ability of a proteinaceous molecule to specifically interfere with the receptor-binding site of apoE ("ARS"), or to interfere with generation of toxic fragments of the apoE molecule having the apoE receptor-binding site, although other general or effector capability may be present in that molecule as well.

Biological activity of an apoE receptor-binding interfering molecule is evidenced by the interference with the binding of apoE with the low density lipoprotein ("LDL") receptor or the LDL receptor-related protein or interference with the toxic effects of apoE peptides incorporating ARS, at least at physiological pH values and ionic strengths. Biological activity of a molecule interfering with generation of toxic fragments is widened by an ability to prevent generation of toxic apoE fragments from full length apoE.

Preferably, biological activity occurs under biological assay conditions; i.e., those conditions within a pH value range of about 5 to about 9, at ionic strengths such as that of distilled water to that of about one molar sodium chloride, and at temperatures of about 4° C. to about 45° C.

"Derivative" refers to subject compounds having one or more amino acid residues or carbohydrate moieties chemically derivatized by reaction of a functional group. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives.

The term "fragment" refers to any subject compound having a composition less than all of the molecule mentioned herein.

The term "glycosaminoglycan" is a general term for any mucopolysaccharide or sulfomucopolysaccharide. This is a general term for a protein-polysaccharide complex obtained from proteoglycans and containing as much as 95% or more polysaccharide. All the known six classes of glycosaminoglycans contain amounts of glucosamine and galactosamine. This class of compounds includes heparin, heparan sulfate, dermatan sulfate and chondroitin sulfate A and C. Heparin is a mucopolysaccharide comprised of D-glucuronic acid and D-glucosamine, both sulfated, in 1,4-α-linkage, of a molecular weight of from about 6000 Da to about 20,000 Da. Heparan sulfate, or heparitin sulfate, is an heteropolysaccharide that has the same repeating disaccharide as heparin but with fewer sulfates and more acetyl groups. Dermatan sulfate, or chondroitin sulfate B, is a mucopolysaccharide containing alternating L-iduronic acid and N-acetyl-D-galactosamine 4-sulfate residues. Chondroitin is a mucopolysaccharide or proteoglycan composed of alternating residues of β-D-glucuronic acid and N-acetylgalactosamine sulfate in alternating β1,3 and β1,4 linkages and are present in the ground substance materials in the extracellular matrix of connective tissue. Chondroitin sulfate A has sulfuric residues esterifying the 4-hydroxyl groups of the galactosamine residues. Chondroitin sulfate C contains sulfuric residues esterifying the 6-hydroxyl groups of the galactosamine residues.

The method of the present invention consists of treating a mammal having a condition associated with toxicity of apolipoprotein E cleavage fragments containing residues 130–169, comprising administering to said mammal a pharmacologically effective amount of compound or a pharmaceutically acceptable salt, derivative or fragment thereof to interfere with the generation of toxic fragments of apoE or the receptor-binding site and toxicity associated with residues 130–169 of the apolipoprotein E molecule in said mammal.

Amino acid residues 130–169 in human apoE encompass an immunoregulatory domain with both cytostatic and cytotoxic activities against interleukin-2 ("IL2")-dependent T cells. The positively charged, leucine-rich sequence, corresponding to amino acids 141–149 (Leu-Arg-Lys-Leu-Arg-Lys-Arg-Leu-Leu; referred to as LRKLRKRLL in single letter amino acid shorthand; SEQ. ID. NO. 1) in the mature protein represents the minimum sequence associated with the receptor-binding site ("ARS"), the heparin-binding site, and cytotoxicity. The present method utilizes compounds to interfere with the ARS. While not being bound by theory, it is believed that the interfering compounds will preferably associate temporarily with the binding site or toxic fragment and, therefore, block access to the binding site to heparin. The association may be from very weak to very strong, depending on the compound utilized. Alternatively, a compound which forms a covalent bond may be utilized.

In one embodiment, the pharmacological composition will preferably comprise a protease inhibitor or a glycosaminoglycan or derivative or fragment hereof along with pharmaceutically acceptable carriers, fillers or excipients. Protease inhibitors, carriers, fillers and excipients are well known in the art. The administering step may comprise administering a pharmacological composition comprising an agent selected from the group consisting of protease inhibitors, heparin, heparan sulfate, dermatan sulfate, dextran sulfate, pentosan polysulfate, polyvinyl sulfate and fragments thereof along with pharmaceutically acceptable carriers, fillers or excipients.

In another embodiment, pharmacological compositions will comprise compounds containing naphthalene sulfonic acids. The naphthalene sulfonic acids can be mono-, di-, or tri-napthalene sulfonic acids and may comprise other substituents as well. Preferably, the naphthalene sulfonic acids will be covalently attached to a phenyl or naphthyl moiety. More preferably, the bond between the naphthalene sulfonic acid and the phenyl or naphthyl group will be a diazo or amide bond. Most preferably, two of the naphthalene sulfonic acid-phenyl molecules will be bonded together through the phenyl groups to form larger, more complex molecules. Examples of such compounds are, but not limited to, ponceau S, direct blue 15, Evan's blue, amaranth, calconcarboxylic acid, suramin sodium, trypan blue, congo red, benzopurpurin 4b, Chicago sky blue 6b and sulfonazo III.

In a further embodiment, pharmacological compositions will comprise compounds having a triphenylmethane core structure comprising at least one carboxylate, sulfonate, benzoic acid or benzene sulfonic acid substituent. In a preferred embodiment, the compound will comprise carboxylic acid substituents. More preferably, the compound will comprise a carboxylic acid substituent on each phenyl moiety of triphenylmethane and most preferably, the compound will be aurintricarboxylic acid. In another preferred embodiment, the phenyl rings of triphenylmethane will comprise at least one benzene sulfonic acid substituent. More preferably, the benzene sulfonic acid will be covalently attached to one of the phenyl rings through a nitrogen bond. Examples of such compounds are, but not limited to, aniline blue, methyl blue, Coomassie brilliant blue R-250, Coomassie brilliant blue G-250 and mixture thereof.

In yet another embodiment, pharmacological compositions will comprise compounds comprising tetrabromophenolsulfonphthalein. Examples of such compounds are, but not limited to, bromophenol blue and bromocresol green.

In another embodiment, pharmacological compositions will comprise compounds chosen from the group consisting essentially of cibacron blue, thiazol yellow G, sulfobromophthalein, biebrich scarlet, or mixtures thereof.

It will be appreciated that pharmacological compositions of the present invention can comprise a mixture of any of the compounds of the present invention along with pharmaceutically acceptable carriers, fillers or excipients.

The methods may be by oral administration of the interfering composition or a pharmaceutically acceptable salt or derivative thereof into said mammal. The methods according to the present invention preferably allows the administration of the interfering molecule in a unitary dose of from about 1 to about 1000 mg. A unitary dose is generally administered from about 1 to about 3 times a day.

The administering step may comprise parenteral administration of the receptor-binding site interfering compound or a pharmaceutically acceptable salt or derivative thereof into said mammal. This administration may be by transdermal administration, subcutaneous injection, intravenous injection, intraperitoneal injection, intramuscular injection, intrasternal injection, intrathecal injection, intracerebroventricular injection, inhalatory spray and infusion techniques.

The method also comprises administering interfering compound or a pharmaceutically acceptable salt or derivative thereof along with a lipophilic compound, such as a lipophilic solvent or carrier. The lipophilic solvent or carrier may be an organic solvent, phosphatidyl choline and cholesterol.

The present method is useful in the treatment of a variety of diseases associated with apoE toxicity including, but not limited to Alzheimer's disease and Alzheimer-related senile dementia, cerebral amyloidosis, coronary heart disease, outcome following head injury or intracerebral hemorrhage, ischemic stroke, normal pressure hydrocephalus, ischemic cerebrovascular disease in end-stage renal disease, glomerulopathy after renal transplantation, diabetic nephropathy, atherosclerosis, and HIV-associated dementia and peripheral neuropathy. Suitable subjects may include those diagnosed as afflicted with Alzheimer's disease or any of the other conditions cited above. The present invention may be employed in treating both familial Alzheimer's disease (late onset and early onset) as well as sporadic Alzheimer's disease. Many Alzheimer's disease patients encountered in practice have no obvious family history and have been classified as sporadic. However, genetic factors in early and late-onset of familial Alzheimer's disease (FAD) are well documented. Late-onset Alzheimer's disease is the classification usually used if the disease is diagnosed to occur after the age of 65 in humans.

It is preferred and contemplated that the methods described herein be used in conjunction with clinical diagnostic information known or described in the art which are used in evaluation of subjects with Alzheimer's disease or suspected to be at risk for developing such disease or other apoE-related diseases.

Studies have shown that apoE fragments ranging from 5 to 22 kDa are present in the post-mortem cerebral spinal fluid from both control patients and patients with AD. The only major band immunoprecipitated by a monoclonal antibody that recognizes the putative toxic domain runs with an apparent molecular weight of about 22 kDa . This fragment likely corresponds to the major apoE thrombin cleavage product. Interference with the production of apoE fragments provides an alternative treatment strategy.

Purified apoE, derived from transfected HEK cells, subjected to thrombin cleavage and separated using gel filtration to collect the 22 kDa fragment, yields enhanced toxicity when tested against primary neurons in culture. The 22 kDa fragments purified from the E4 isoform is more toxic than E3-derived fragments. The putative toxic site is closely associated with one of two well-characterized heparin binding domains associated with residues 141–147 of apoE.

The density of four positively charged amino acid residues in the 141–149 domain clearly make a significant contribution to apoE peptide toxicity. Consistent with this conclusion is the ablation of peptide-mediated toxicity by the polyanionic glycosaminoglycans ("GAG") heparin, heparan sulfate and chondroitin sulfate. Furthermore, not all GAGs show inhibition of toxicity.

In one embodiment, the site-interfering compound may be a glycosaminoglycan or derivative or fragment thereof. It is known that glycosaminoglycans are products capable of being obtained by extraction from animal tissues. Certain of these glycosaminoglycans have very advantageous anticoagulating and antithrombotic properties. Typical products of this family are heparin, its cleavage products and their derivatives, as well as heparan sulfate and dermatan sulfate. However, preferred methods of the present invention will utilize compounds without potent anticoagulant properties.

In particular, it is known that dermatan sulfate is a family of polymers with a variable degree of polymerization, formed of repeating units consisting of a uronic acid group (iduronyl or glucuronyl) and of an acetyl 4-sulphated galactosaminyl group (H. W. Stuhlsatz, "The Methodology of Connective Tissue Research", (1976), 137–146). Natural dermatan sulfate has a molecular mass of between 2×104 and $4\times10^4$D. This product is particularly advantageous as an anticoagulant and antithrombin (F. Fernandez et al., British Journal of Haematology, (1986), 64, 309–317). The heparin-binding site interfering compound may be a glycosaminoglycan or derivative or fragment thereof with a molecular mass of between 2×101 and $4\times10^5$D.

It is known that the main heparin chain is constructed in two stages. In a first stage, heparin is biosynthesized from a precursor proteoglycan whose polysaccharide part consists of a family of polymers with a variable degree of polymerization formed from repeating beta -D-glucuronyl-1,4- alpha -N-acetyl-D-glucosaminyl-(1,4) disaccharide units. This polysaccharide part is generally called N-acetylheparosan (Navia, J., *AnaL Biochem.* 135:134–140 (1983)). This first stage of biosynthesis is the only time when it is truly possible to speak of a "disaccharide unit" because the second stage of the biosynthesis will profoundly change this simple skeleton ("L'heparin, fabrication, structure, properties, analyses", J. P. Duelos, (1984) pp. 81–83, Masson Ed.-France).

Natural heparin resulting from biosynthesis is a polysaccharide consisting of molecules of glucuronic acid and of iduronic acid (uronic acids), optionally sulphated in position 2, combined with molecules of glucosamine, optionally sulphated in position 6 and sulphated or acetylated on the amine in position 2. The heparin-binding site interfering compound may be a compound derived from natural heparin.

The natural heparin used as the starting material can be standard heparin or any other commercially available heparin, provided that it has a good quality. A sodium salt of heparin may be used, even if other salts can conveniently be used. It is preferable that starting heparin be anhydrous, hence a preliminary dehydration is properly performed, for example, at a temperature of from about 500 to about 60° C. The interfering compound may be derived from natural heparin through cleavage with enzymes or through other chemical means.

In one embodiment, the ARS blocking compound may be, for example, dermatan sulfate (#03125 and #03120), heparan sulfate 1 (#03100), heparan sulfate 2 (#03400), LP heparin fraction (#03010), and HP heparin fraction (#03020) (all from Celsus Laboratories, Inc., Cincinnati, Ohio). Other compounds include heparin sulfate (Product Nos. H5393, H9902, H7640, H9637, and H7641) and heparin (Product Nos. H0880, H8398, and H0878) (all from Sigma Chemical Co., St. Louis, Mo.).

In another embodiment, the ARS blocking compound may comprise compounds containing naphthalene sulfonic acids. The naphthalene sulfonic acids can be mono-, di-, or tri-napthalene sulfonic acids and may comprise other substituents as well. Preferably, the naphthalene sulfonic acids will be covalently attached to a phenyl or naphthyl moiety. More preferably, the bond between the naphthalene sulfonic acid and the phenyl or naphthyl group will be a diazo or amide bond. Most preferably, two of the naphthalene sulfonic acid-phenyl molecules will be bonded together through the phenyl groups to form larger, more complex molecules. Examples of such compounds are, but not limited to, ponceau S, direct blue 15, Evan's blue, amaranth, calconcarboxylic acid, suramin sodium, trypan blue, congo red, benzopurpurin 4b, Chicago sky blue 6b and sulfonazo III.

In a further embodiment, the ARS blocking compound may comprise compounds having a triphenylmethane core structure comprising at least one carboxylate, sulfonate, benzoic acid or benzene sulfonic acid substituent. In a preferred embodiment, the compound will comprise carboxylic acid substituents. More preferably, the compound will comprise a carboxylic acid substituent on each phenyl moiety of triphenylmethane and most preferably, the compound will be aurintricarboxylic acid. In another preferred embodiment, the phenyl rings of triphenylmethane will comprise at least one benzene sulfonic acid substituent. More preferably, the benzene sulfonic acid will be covalently attached to one of the phenyl rings through a nitrogen bond. Examples of such compounds are, but not limited to, aniline blue, methyl blue, Coomassie brilliant blue R-250, Coomassie brilliant blue G-250 and mixture thereof.

In yet another embodiment, the ARS blocking compound may comprise compounds comprising tetrabromophenolsulfonphthalein. Examples of such compounds are, but not limited to, bromophenol blue and bromocresol green.

In another embodiment, the ARS blocking compound may comprise compounds chosen from the group consisting essentially of cibacron blue, thiazol yellow G, sulfobromophthalein, biebrich scarlet, or mixtures thereof.

It will be appreciated that the ARS blocking compound of the present invention may comprise a mixture of any of the compounds of the present invention along with pharmaceutically acceptable carriers, fillers or excipients.

The pharmaceutical compositions of the present invention can be formulated for oral, sublingual, subcutaneous, intravenous, transdermic or rectal administrations in dosage units and in admixture with pharmaceutical excipients or vehicles. Convenient dosage forms include, among those for oral administration, tablets, powders, granulates, and, among those for parenteral administration, solutions especially for transdermal administration, subcutaneous injection, intravenous injection, intraperitoneal injection, intramuscular injection, intrasternal injection, intrathecal injection, inhalatory spray, and infusion techniques.

The pharmaceutical compositions of the present invention are administered, in the above mentioned forms and routes, to animals and man in case of a pathological increase in toxicity of apoE fragments containing the residue sequence 130–169, particularly in the treatment of Alzheimer's disease.

The daily amount in the aforesaid indications may range from 0.1 to 100 mg/kg and each unitary dose may contain from 1 to 1000 mg of the active ingredient. Such unitary dose can be administered from 1 to 3 times a day for the treatment of dementia disorders and atherosclerosis.

The dosage can vary widely as a function of the age, weight and state of health of the patient, the nature and the severity of the ailment, as well as of the administration route. These doses can naturally be adjusted for each patient according to the results observed and the blood analyses previously carried out.

The following examples illustrate and explain the present invention but should not be taken as limiting the present invention in any regard.

EXAMPLE 1

Since the 22 kDa fragment contains the domain associated with toxicity and corresponds to the major N-terminal proteolytic fragment of apoE, assessment of the efficacy of a compound can first be screened by measuring the inhibition of the 22 kDa toxicity in vitro. The 22 kDa thrombolytic cleavage fragment product of apoE is neurotoxic and is purified from medium of HEK cells transfected with the gene for human apoE4. Neuronal toxicity is then assessed using dissociated embryonic chick sympathetic neurons in 96 well microtiter plates. Following the addition of the fragments, the cultures are incubated overnight. Viability is then assessed by vital dye staining.

EXAMPLE 2

Effects of apoE 22 kDa Peptides on Sympathetic Neurons in Culture.

Transfected HEK cells are cultured as previously described (LaDu, M. J., et al., *J. Biol. Chem.* 258:12348–54 (1983)). The apoE is concentrated from conditioned medium by ultrafiltration (10 kDa cut-off membrane, Amicon) followed by heparin column chromatography (heparin-coupled agarose beads, Sigma). The purified apoE is then digested with thrombin and the resulting fragments are separated by HPLC gel filtration chromatography (Bio SEC-Bio Rad). After buffer exchange with centricon 10 (Amicon) and lyophilization, the purified 22 kDa fragment is subjected to amino acid analysis. For neurotoxicity studies, lumbar sympathetic chain ganglia are isolated from embryonic day nine chicken embryos (Spafas, Inc., Roanoke, Ill.) under sterile conditions in unsupplemented Ham's F12 medium (Sigma). The dissected chains are exposed to trypsin (0.25%) for 20 minutes at 37° C. The trypsin is inactivated by adding fetal bovine serum. The chains are washed three times with medium and then triturated with flamed Pasteur pipettes to dissociate the cells. The cells are resuspended in Neurobasal medium (Gibco) and plated into 96-well plates pretreated with poly-ornithine. Dishes are incubated at 37° C. with 5% $CO_2$/95% air. Following overnight incubation, the cells are treated with dermatan sulfate (#03125, Celsus Laboratories, Inc., Cincinnati, Ohio), diluted in F12 medium supplemented with 100μM putrescine, 20 nM progesterone, 100 μg/ml human transferrin, 30 nM selenium and 1% antibiotics (penicillin-streptomycin). The average molecular weight is approximately 35 kDa. The neuronal cells are preincubated for 10 min. at 37° C. with 4 μM of the dermatan sulfate. The toxic fragments are added to the culture medium. Controls use the corresponding vehicle. After overnight incubation, the cells are labeled with a vital dye (5-carboxyfluorescein diacetate, acetoxymethyl ester, Molecular Probes, Eugene, OR) for 30 minutes. The wells are washed with fresh F12 medium and images of the stained cells are collected from each well by using a Diaphot inverted fluorescence microscope connected to a Macintosh IIfx computer equipped with a Framegrabber video card. The number of labeled neurons is quantified from the stored images with NIH Image software (version 1.57). The results show the number of cells surviving following overnight exposure to different concentrations of either the E3- or E4-derived 22 kDa fragment. Those treated with the dermatan sulfate show toxicity is completely ablated.

EXAMPLE 3

Same as above only neuronal toxicity is tested with heparan sulfate (#03105, Celsus Laboratories, Inc., Cincinnati, Ohio).

EXAMPLE 4

Same as above only neuronal toxicity is tested with the high potency heparin fraction (#03025, Celsus Laboratories, Inc., Cincinnati, Ohio).

EXAMPLE 5

Results of in vitro experiments showing interference effect of a protease inhibitor mixture.

Full-length apoE4 (8 μM) was added to primary chick sympathetic neurons in cultures using the procedure of Example 1 in the presence and absence of a mixture of protease inhibitors obtained from Sigma Chemical Co.:

| protease inhibitor | concentration |
|---|---|
| aprotinin | 1.5 ± 0.5 μg/ml |
| leupeptin | 1.5 ± 0.5 μg/ml |
| pepstatin A | 1.5 ± 0.5 μg/ml |
| antipain | 1.5 ± 0.5 μg/ml |

The protease inhibitor mixture was found to significantly reduce the toxicity of the apoE and to reduce the production of apoE fragments (based on Western blotting). The same protease inhibition mixture did not block the toxicity of the apoE fragment or the long tandem apoE peptide. Therefore, the method of interfering is likely not due to interfering with the binding of apoE fragments to the receptor, but due to prevention of generation of toxic fragments.

EXAMPLE 6

Protection of Sympathetic Neurons Against Toxic apoE Fragments by Various Compounds.

Transfected HEK cells were cultured as previously described (LaDu, M. J., et el., *J. Biol. Chem.*258:12348–54 (1983).) The apoE was concentrated from conditioned medium by ultrafiltration (10 kDa cut-off membrane, Amicon) followed by heparin column chromatography (heparin-coupled agarose beads, Sigma). The purified apoE was then digested with thrombin and the resulting fragments separated by HPLC gel filtration chromatography (Bio SEC-Bio Rad). After buffer exchange and lyophilization, the purified 22 kDa fragment was subjected to amino acid analysis. For neurotoxicity studies, lumbar sympathetic chain ganglia were isolated from embryonic day nine chicken embryos (Spafas, Inc., Roanoke, Ill.) under sterile conditions in unsupplemented Ham's F12 medium (Sigma). The dissected chains were exposed to trypsin (0.25%) for 20 minutes at 37° C. The trypsin was inactivated by addition of fetal bovine serum. The chains were washed three times with medium and then triturated with flamed Pasteur pipettes to dissociate the cells. The cells were resuspended in Neurobasal medium (Gibco) and plated into 96-well plates pretreated with poly-ornithine. Dishes were incubated at 37° C. with 5% $CO_2$/95% air. Following overnight incubation, the cells were treated with a range of concentrations of various compounds diluted in F12 medium supplemented with 100 μM putrescine, 20 nM progesterone, 100 μg/ml human transferrin, 30 nM selenium and 1% antibiotics (penicillin-streptomycin). The neuronal cells were preincubated for 10 min at 37° C. with a predetermined concentration of compound. The toxic fragments were then added to the culture medium while controls used the corresponding vehicle without the toxic fragments. After overnight incubation, the cells were labeled with a vital dye (5-carboxyfluorescein diacetate, acetoxymethyl ester, Molecular Probes, Eugene, Oreg.) for 30 minutes. The wells were washed with fresh F12 medium and images of the stained cells were collected from each well using a Diaphot inverted fluorescence microscope connected to a Macintosh IIfx computer equipped with a Framegrabber video card. The number of labeled neurons was quantified from the stored images with NIH Image software (version 1.57).

The results shown in Table 1 are expressed as $C_{50}$, the concentration required prevent 50% cell death as compared to control.

TABLE 1

| Compound | $C_{50}$ ($\mu$M) |
|---|---|
| potassium polyvinyl sulfate | 0.035 |
| pentosan sulfate | 1.5 |
| dextran sulfate (5 kDa) | 0.8 |
| heparan sulfate | 1.0 |
| ponceau S | 5 |
| direct blue 15 | 18 |
| Evan's blue | 8 |
| amaranth | 25 |
| calconcarboxylic acid | 10 |
| suramin sodium | 5 |
| trypan blue | 20 |
| congo red | 25 |
| benzopurpurin 4b | 50 |
| Chicago sky blue 6b | 15 |
| sulfonazo III | 45 |
| aurintricarboxylic acid | 11 |
| aniline blue | 25 |
| methyl blue | 20 |
| Coomassie brilliant blue G-250 | 40 |
| Coomassie brilliant blue R-250 | 35 |
| light green S.F. yellowish | 40 |
| bromophenol blue | 16 |
| bromocresol green | 25 |
| cibacron blue | 20 |
| thiazol yellow G | 25 |
| sulfobromophthalein | 32 |
| biebrich scarlet | 40 |

The foregoing discussion discloses and describes merely exemplary embodiments of the present invention. One skilled in the art will readily recognize from such discussion, and from the accompanying claims, that various changes, modifications and variations can be made therein without departing from the spirit and scope of the invention as defined in the following claims.

All references cited herein are incorporated by reference as if fully set forth herein.

What is claimed is:

1. A method of preventing toxicity caused by a peptide fragment of apolipoprotein E having a molecular weight of at least 5 kD to a cell comprising treating said cell with a compound, wherein the compound comprises a tetrabromophenolsulfonphthalein.

2. The method of claim 1, wherein the compound is selected from the group consisting of bromophenol blue, bromocresol green and mixtures thereof.

3. A method of preventing toxicity caused by a peptide fragment of apolipoprotein E having a molecular weight of at least 5 kD to a cell comprising treating said cell with a compound, wherein the compound is selected from the group consisting of cibacron blue, thiazol yellow G, sulfobromophthalein, biebrich scarlet and mixtures thereof.

4. The method of claim 1, wherein inhibiting said toxicity comprises inhibiting binding of peptide fragments of apolipoprotein E to a cell.

5. The method of claim 1, wherein the fragments of apolipoprotein E comprise residues 141–147 of apolipoprotein E.

6. The method of claim 1, wherein inhibiting apolipoprotein E toxicity comprises inhibiting production of a peptide fragment of apolipoprotein E comprising residues 141–147 of apolipoprotein E.

7. A method of treating a mammal having a condition associated with toxicity caused by a peptide fragment of apolipoprotein E having a molecular weight of at least 5 kD, comprising administering a composition comprising a pharmacologically effective amount of a compound, wherein the compound comprises a tetrabromophenolsulfonphthalein.

8. The method of claim 7, wherein the compound is selected from the group consisting of bromophenol blue, bromocresol green and mixtures thereof.

9. A method of treating a mammal having a condition associated with toxicity caused by a peptide fragment of apolipoprotein E having a molecular weight of at least 5 kD, comprising administering a composition comprising a pharmacologically effective amount of a compound, wherein the compound is selected from the group consisting of cibacron blue, thiazol yellow G, sulfobromophthalein, biebrich scarlet and mixtures thereof.

10. The method of claim 7, wherein inhibiting toxicity caused by apolipoprotein E comprises inhibiting binding of peptide fragments of apolipoprotein E to a cell, wherein the peptide fragments of apolipoprotein E have a molecular weight of at least 5 kD.

11. The method of claim 10, wherein the fragments of apolipoprotein E comprise residues 141–147 of apolipoprotein E.

12. The method of claim 7, wherein inhibiting apolipoprotein E toxicity comprises inhibiting production of a peptide fragment of apolipoprotein E comprising residues 141–147 of apolipoprotein E wherein the peptide fragment has a molecular weight of at least 5 kD.

13. The method of claim 7, wherein the condition is Alzheimer's-type senile dementia.

14. The method of claim 7, wherein the condition is a condition associated with cerebral amyloidosis.

15. The method of claim 7, wherein the condition is hyperlipidemia.

16. The method of claim 7, wherein the condition is selected from the group consisting of coronary heart disease, atherosclerosis, head injury, ischemic stroke, intracerebral hemorrhage, normal pressure hydrocephalus, HIV-associated dementia and HIV-associated peripheral neuropathy.

17. The method of claim 9, wherein inhibiting toxicity caused by apolipoprotein E comprises inhibiting binding of peptide fragments of apolipoprotein E to a cell, wherein the peptide fragments of apolipoprotein E have a molecular weight of at least 5 kD.

18. The method of claim 7, wherein the fragments of apolipoprotein E comprise residues 141–147 of apolipoprotein E.

19. The method of claim 9, wherein inhibiting apolipoprotein E toxicity comprises inhibiting production of a peptide fragment of apolipoprotein E comprising residues 141–147 of apolipoprotein E wherein the peptide fragment has a molecular weight of at least 5 kD.

20. The method of claim 9, wherein the condition is Alzheimers-type senile dementia.

21. The method of claim 9, wherein the condition is a condition associated with cerebral amyloidosis.

22. The method of claim 9, wherein the condition is hyperlipidemia.

23. The method of claim 9, wherein the condition is selected from the group consisting of coronary heart disease, atherosclerosis, head injury, ischemic stroke, intracerebral hemorrhage, normal pressure hydrocephalus, HIV-associated dementia and HIV-associated peripheral neuropathy.

* * * * *